(12) United States Patent
Frigg et al.

(10) Patent No.: US 8,221,419 B2
(45) Date of Patent: Jul. 17, 2012

(54) INTRAMEDULLARY NAIL

(75) Inventors: Robert Frigg, Bettlach (CH); Marcel Fuhrer, Deitingen (CH)

(73) Assignee: Synthes USA, LLC, West Chester, PA (US)

( * ) Notice: Subject to any disclaimer, the term of this patent is extended or adjusted under 35 U.S.C. 154(b) by 968 days.

(21) Appl. No.: 11/365,998

(22) Filed: Feb. 28, 2006

(65) Prior Publication Data

US 2006/0235395 A1   Oct. 19, 2006

(51) Int. Cl.
*A61B 17/72* (2006.01)

(52) U.S. Cl. .......................................... 606/63; 606/68

(58) Field of Classification Search .............. 606/62–68, 606/96, 98, 309, 313, 314, 329; 623/23.23; 411/55, 57.1, 59
See application file for complete search history.

(56) References Cited

U.S. PATENT DOCUMENTS

| | | | |
|---|---|---|---|
| 2,834,342 A | 5/1958 | Yost | |
| 3,255,747 A | 6/1966 | Cochran et al. | |
| 3,433,220 A | 3/1969 | Zickel | |
| 4,095,591 A | 6/1978 | Graham, Jr. et al. | |
| 4,103,683 A | 8/1978 | Neufeld | |
| 4,172,452 A | 10/1979 | Forte et al. | |
| 4,274,163 A | 6/1981 | Malcom et al. | |
| 4,438,762 A | 3/1984 | Kyle | |
| 4,494,535 A | 1/1985 | Haig | |
| 4,612,920 A | 9/1986 | Lower | |
| 4,621,628 A | 11/1986 | Brudermann | |
| 4,622,959 A | 11/1986 | Marcus | |
| 4,628,920 A * | 12/1986 | Mathys et al. | 606/62 |
| 4,657,001 A | 4/1987 | Fixel | |
| 4,697,585 A | 10/1987 | Williams | |
| 4,705,027 A | 11/1987 | Klaue | |
| 4,754,749 A | 7/1988 | Tsou | |
| 4,776,330 A | 10/1988 | Chapman et al. | |
| 4,791,918 A | 12/1988 | Von Hasselbach | |
| 4,817,591 A | 4/1989 | Klaue | |
| 4,928,679 A * | 5/1990 | Chagneau et al. | 606/62 |
| 4,973,332 A | 11/1990 | Kummer | |
| 4,978,349 A * | 12/1990 | Frigg | 606/67 |

(Continued)

FOREIGN PATENT DOCUMENTS

CH     668 173     12/1988

(Continued)

OTHER PUBLICATIONS

"shape." Merriam-Webster Online Dictionary. 2009. Merriam-Webster Online. Sep. 24, 2009 <http://www.merriam-webster.com/dictionary/shape>.*

(Continued)

*Primary Examiner* — Eduardo C Robert
*Assistant Examiner* — Steven Cotroneo
(74) *Attorney, Agent, or Firm* — Fay, Kaplun & Marcin, LLP

(57) ABSTRACT

The intramedullary nail has a longitudinal axis, a proximal end, a distal end, at least one hole that extends transversely to the longitudinal axis and is situated in a plane with a defined diameter to accommodate a locking element, as well as a longitudinal slot extending in the plane parallel to the longitudinal axis. In the unexpanded state of the intramedullary nail the longitudinal slot has a width b, measured perpendicularly to the plane in the region outside of the holes, said slot being maximum 0.6 times that of the smallest defined diameter of the holes.

18 Claims, 6 Drawing Sheets

U.S. PATENT DOCUMENTS

| | | |
|---|---|---|
| 5,032,125 A | 7/1991 | Durham et al. |
| 5,041,114 A | 8/1991 | Chapman et al. |
| 5,041,115 A | 8/1991 | Frigg et al. |
| 5,120,171 A | 6/1992 | Lasner |
| 5,167,663 A | 12/1992 | Brumfield |
| 5,176,681 A | 1/1993 | Lawes et al. |
| 5,224,805 A * | 7/1993 | Moretti et al. ............ 411/30 |
| 5,300,074 A | 4/1994 | Frigg |
| 5,312,406 A | 5/1994 | Brumfield |
| 5,364,398 A | 11/1994 | Chapman et al. |
| 5,454,813 A | 10/1995 | Lawes |
| 5,484,439 A | 1/1996 | Olson et al. |
| 5,549,610 A | 8/1996 | Russell et al. |
| 5,573,536 A | 11/1996 | Grosse et al. |
| 5,578,035 A | 11/1996 | Lin |
| 5,591,168 A | 1/1997 | Judet et al. |
| 5,658,287 A | 8/1997 | Hofmann et al. |
| 5,658,339 A | 8/1997 | Tronzo et al. |
| 5,713,901 A | 2/1998 | Tock |
| 5,713,902 A | 2/1998 | Friedl |
| 5,728,099 A | 3/1998 | Tellman et al. |
| 5,741,256 A | 4/1998 | Bresina |
| 5,772,662 A | 6/1998 | Chapman et al. |
| 5,908,422 A | 6/1999 | Bresina |
| 5,928,235 A | 7/1999 | Friedl |
| 5,935,127 A | 8/1999 | Border |
| 5,976,139 A | 11/1999 | Bramlet |
| 6,010,506 A | 1/2000 | Gosney et al. |
| 6,059,785 A | 5/2000 | Schavan et al. |
| 6,123,708 A * | 9/2000 | Kilpela et al. ............ 606/62 |
| 6,126,661 A | 10/2000 | Faccioli et al. |
| 6,187,007 B1 | 2/2001 | Frigg et al. |
| 6,296,645 B1 | 10/2001 | Hover et al. |
| 6,302,627 B1 * | 10/2001 | Reichelt ............ 411/33 |
| 6,454,810 B1 | 9/2002 | Lob |
| 6,676,348 B2 * | 1/2004 | Hoppe ............ 411/48 |
| 6,846,141 B2 * | 1/2005 | Heinzelmann et al. ...... 411/57.1 |
| 7,182,765 B2 | 2/2007 | Roth et al. |
| 2002/0151898 A1 | 10/2002 | Sohngen et al. |
| 2002/0173792 A1 | 11/2002 | Severns et al. |
| 2003/0069581 A1 | 4/2003 | Stinson et al. |
| 2003/0114855 A1 | 6/2003 | Wahl et al. |
| 2006/0064095 A1 | 3/2006 | Senn et al. |
| 2006/0111716 A1 | 5/2006 | Schlienger et al. |
| 2006/0149248 A1 | 7/2006 | Schlienger et al. |
| 2006/0161155 A1 | 7/2006 | Schlienger et al. |
| 2006/0189988 A1 | 8/2006 | Schlienger et al. |
| 2006/0241605 A1 | 10/2006 | Schlienger et al. |

FOREIGN PATENT DOCUMENTS

| | | | |
|---|---|---|---|
| CH | 674 613 | | 6/1990 |
| DE | 196 29 011 A1 | | 1/1998 |
| DE | 199 45 611 A1 | | 9/2001 |
| EP | 0 251 583 A2 | | 1/1988 |
| EP | 0 321 170 B1 | | 6/1989 |
| EP | 0 381 462 A2 | | 8/1990 |
| EP | 0 411 273 A1 | | 2/1991 |
| EP | 0 471 418 A1 | | 2/1992 |
| EP | 0 838 199 A1 | | 4/1998 |
| EP | 0 845 245 A2 | | 6/1998 |
| EP | 0 853 923 A1 | | 7/1998 |
| EP | 0 919 200 A1 | | 6/1999 |
| EP | 0 968 685 A2 | | 6/1999 |
| EP | 1 053 718 A1 | | 11/2000 |
| EP | 1 214 914 A2 | | 6/2002 |
| EP | 1 260 188 A1 | | 11/2002 |
| FR | 2 784 283 | | 4/2000 |
| GB | 2209947 A | | 6/1989 |
| JP | 09-066059 | | 3/1997 |
| JP | 09-066060 | | 3/1997 |
| JP | 09-066061 | | 3/1997 |
| JP | 11-137566 | | 5/1999 |
| JP | 2000-051224 | | 2/2000 |
| JP | 2000-051225 | | 2/2000 |
| JP | 2000051225 | * | 2/2000 |
| JP | 2000-342596 | | 12/2000 |
| WO | WO 93/15679 | | 8/1993 |
| WO | WO 96/15737 | | 5/1996 |
| WO | WO 97/37606 | | 10/1997 |
| WO | WO 98/05263 | | 2/1998 |
| WO | WO 98/30164 | | 7/1998 |
| WO | WO 98/41161 | | 9/1998 |
| WO | WO 98/46169 | | 10/1998 |
| WO | WO 00/67653 | | 11/2000 |
| WO | WO 02/060331 | | 8/2002 |
| WO | WO 03/015649 | | 2/2003 |

OTHER PUBLICATIONS

International Search Report for International Application No. PCT/CH03/00591, mailed May 26, 2004, German language version.

International Search Report for International Application No. PCT/CH03/00591, mailed May 26, 2004, English language translation of the German language version.

* cited by examiner

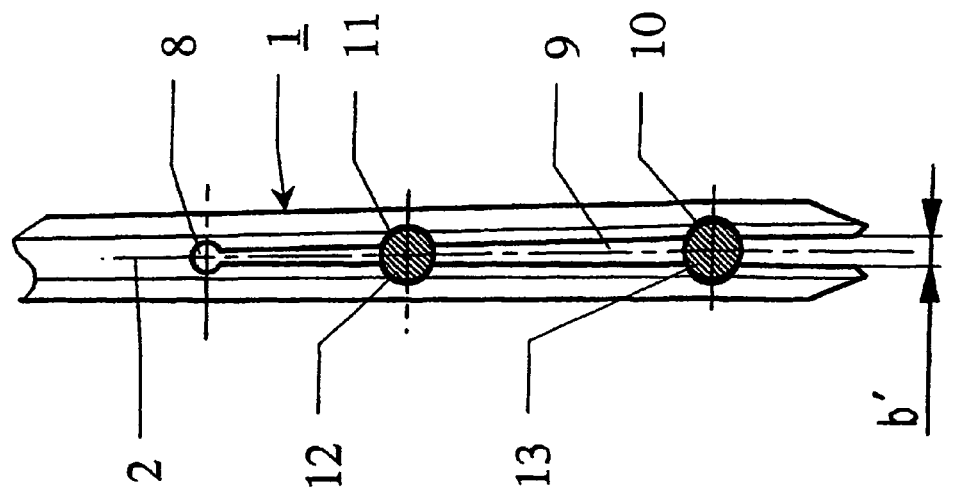
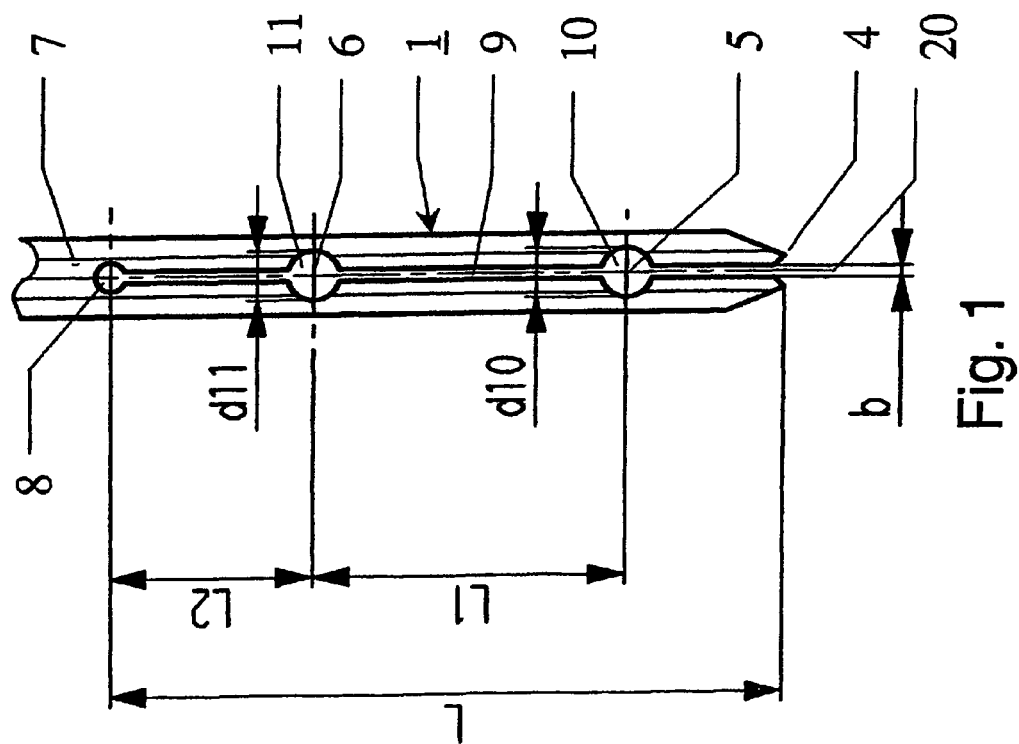

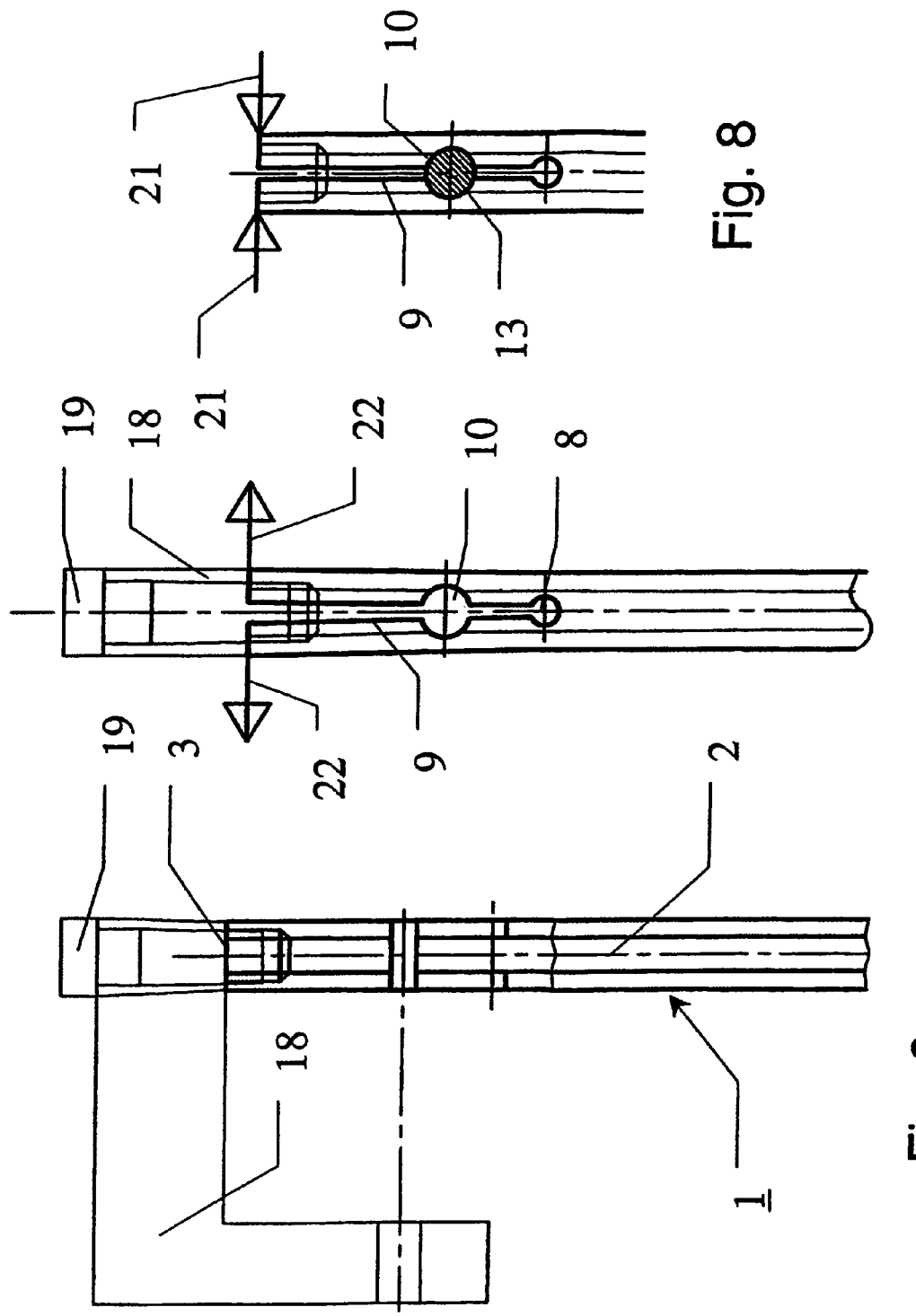

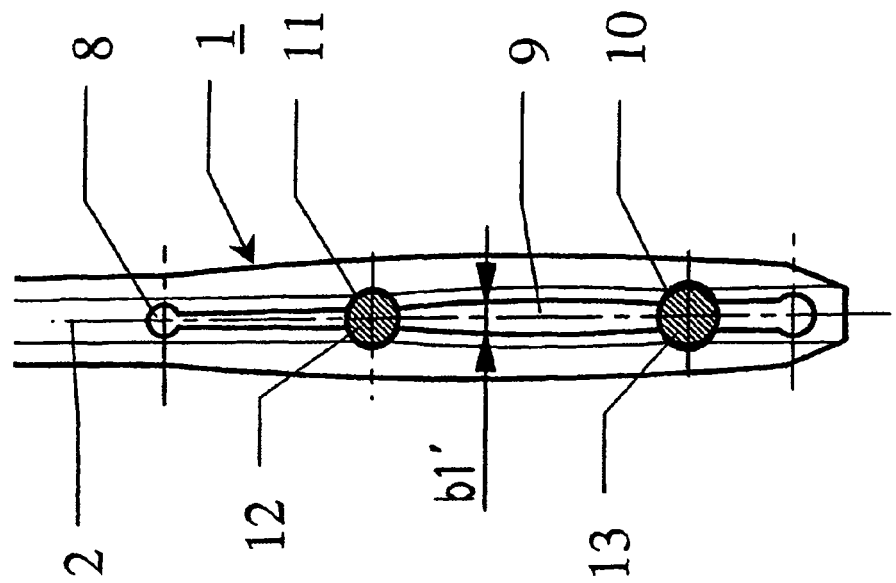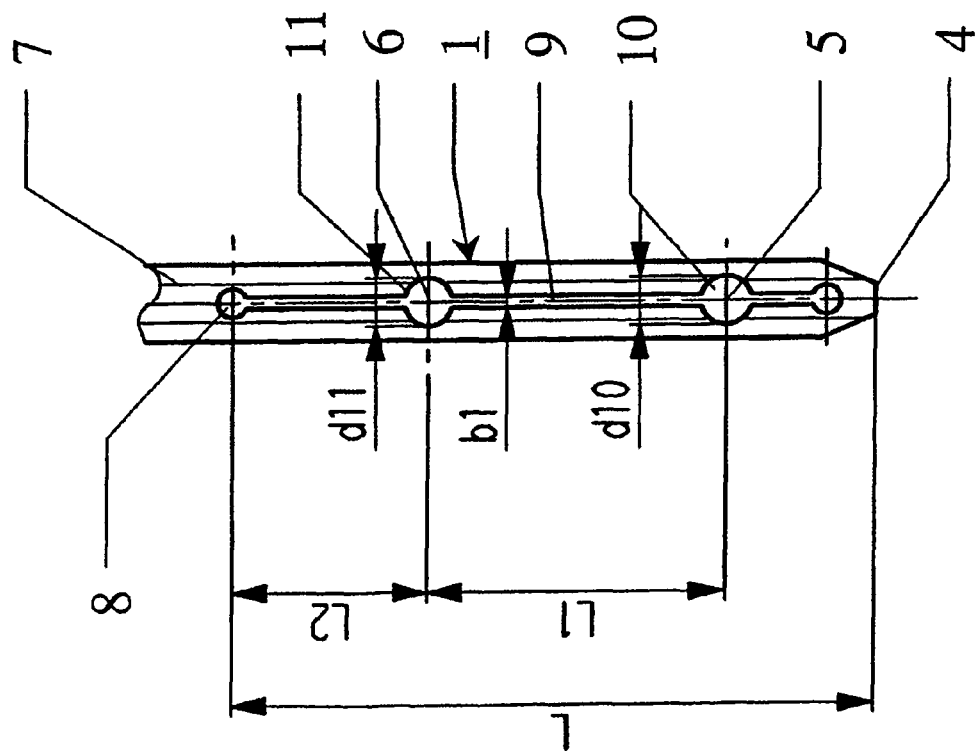

INTRAMEDULLARY NAIL

RELATED APPLICATION DATA

The present application is a continuation of the U.S. National Stage designation of co-pending International Patent Application No. PCT/CH2003/000591, filed Aug. 29, 2003, the entire content of which is expressly incorporated herein by reference thereto.

FILED OF INVENTION

The invention concerns an intramedullary nail for use in orthopaedic surgery.

BACKGROUND OF THE INVENTION

From CH-A5 668 173 to Klaue, an intramedullary nail having a longitudinal slot at its distal end is known. This known intramedullary nail is intended to be introduced into the medullary space only after the implantation of the associated locking element (a screw or a bolt), where, with its slotted tip, it contacts the locking screw, which expands the slot such that the intramedullary nail can slide over the locking screw up to its end position. Thus, the initially set locking screw serves as a targeting aid for the intramedullary nail to be subsequently implanted. To enable this, the longitudinal slot of this known intramedullary nail is relatively wide in comparison with the diameter of the locking screw, because the longitudinal slot could otherwise not open. However, the relatively wide longitudinal slot has two disadvantages: first, the strength of the tip of the intramedullary nail is greatly reduced, and second, the intramedullary nail may move axially relative to the locking screw at any time.

The present invention is intended to remedy these problems. The object of the invention is to produce a slotted intramedullary nail, that after the introduction of the locking element does not permit relative axial movements.

SUMMARY OF THE INVENTION

This objective is achieved by the invention with an intramedullary nail having a nail body having a central longitudinal axis, a proximal end, and a distal end. At least one hole extends through the nail body and has a central hole axis transverse to the longitudinal axis of the nail body. The at least one hole has a diameter configured to accommodate a locking element, and the central hole axis is located in a first plane. A longitudinal slot extends through the nail body in the first plane parallel to the longitudinal axis, the longitudinal slot having an unexpanded width b measured perpendicularly to the first plane. An expansion limiting structure is formed integral with the nail body for limiting expansion of the longitudinal slot, and the maximum unexpanded width b of the slot is 0.6 times the diameter of the at least one hole.

The advantages of the intramedullary nail according to the invention are manifold:

a) the reduced rigidity of the nail facilitates implantation;

b) when using locking bolts, the diameters of which are slightly greater than the transverse hole in the intramedullary nail, due to the elastic deformation of the nail, the bolts can be clamped, leading to a better anchoring of the nail in the bone;

c) due to the elasticity in the region of the slot, where the locking holes are also situated, in the case of small nail diameters, locking bolts with larger diameters can be used (in the case of conventional nails this would lead to a reduction of the cross-section of the nail, due to large holes);

d) due to the elasticity, caused by the slot, detrimental stress concentration can be reduced in the region of the locking holes;

e) no relative longitudinal movement is possible between the intramedullary nail and the locking screw without a plastic deformation of the intramedullary nail or of the locking screw taking place; and f) the locking element(s) is (are) clamped without any clearance and are secured against angular misalignment or any movement.

In the case of a particular embodiment, the width of the slot b of the intramedullary nail is maximum 0.6 times, and preferably maximum 0.5 times that of the smallest defined diameter of the holes. In still another embodiment, the width b of the slot is a maximum of 0.4 times that of the smallest defined diameter of the holes. By virtue of this, the intramedullary nail is flexible in an optimum manner during the introduction and the locking elements are fixed and clamped angularly stable in an optimum manner.

In the case of another embodiment the number of holes 10, 11 is two, while the diameter d10 of the hole closer to the opening of the longitudinal slot is smaller than diameter d11 of the other hole. Due to this, locking elements with larger dimensions can be used, resulting in fewer broken bolts.

The longitudinal slot of the intramedullary nail has a length of L, that is preferably 10 times, typically 15 times that of the smallest defined diameter d10 of the holes. Due to this, the intramedullary nail is flexible when being introduced.

The width b of the slot should preferably be constant over the entire length L of the slot. The result of this is a simplified manufacturing technology as well as a minimal weakening of the intramedullary nail with the smallest possible slot width.

The slot can be protected, for example in the form of a dovetail, that limits the expansion of the slot within reason. This will prevent a possible excessive expansion of the slot.

In the case of a preferred embodiment, the longitudinal slot commences at the proximal end of the intramedullary nail. In contrast to an intramedullary nail with the conventional distal slot, an intramedullary nail with a proximal slot has the advantage that it can be elastically pre-expanded by means of a suitable driving instrument, so that the locking element could be introduced into the intramedullary nail through the target yoke of the instrument. After removing the instrument, the proximal slot closes again, due to which the locking elements are firmly clamped in the intramedullary nail.

In the case of a further embodiment, the longitudinal slot terminates neither at the distal end nor at the proximal end of the intramedullary nail. This enclosed version has the advantage, that an unintentionally large expansion of the distal (or proximal) end of the intramedullary nail is prevented, particularly for intramedullary nails with a small diameter. Such an expansion may lead to stress concentration at the end of the slot. If the slot is closed at both ends, the locking elements can be clamped even firmer.

The intramedullary nail may have a hollow construction in the direction of the longitudinal axis.

The locking elements to be introduced into the holes of the intramedullary nail have a defined diameter, which is preferably greater than the defined diameter of the associated hole. The defined diameter of the locking element can, however, be the same as the defined diameter of the associated hole. The latter execution has the advantage, that the rigidity of the nail is reduced and the implanting is simplified.

The defined diameter of the locking element can, however, be at least 1.1 times, preferably 1.2 times that of the defined diameter of the associated hole. In the case of this embodiment, larger locking elements can be used while retaining the cross-section of the nail and the breaking of the locking elements can be prevented in the case of small intramedullary nails.

The diameter of the locking element, introduced closer to the opening of the longitudinal slot, is preferably larger than the diameter of the other locking elements.

By introducing the locking element into the hole, the intramedullary nail will be elastically expanded in the region of the longitudinal slot. The length L of the longitudinal slot should preferably be so chosen, that when the locking element is introduced the intramedullary nail is deformed only within the elastic range.

In the case of a further embodiment, the intramedullary nail has an additional locking hole, extending at right angle to the plane of the holes. This results in an increase of the rigidity of the nail after its implanting and the setting of the locking elements in the plane of both holes. The elasticity of the nail is achieved by the longitudinal slot and simplifies the implanting of the nail. However, once the nail is implanted, the return of the rigidity is desirable, particularly in the case of thin nails.

BRIEF DESCRIPTION OF THE DRAWINGS

The invention and developments of the invention are explained in detail below based on partly schematic illustrations of several embodiments, wherein:

FIG. 1 shows a partial longitudinal section through an intramedullary nail slotted at the distal end;

FIG. 2 shows a partial longitudinal section according to FIG. 1 with inserted locking elements;

FIG. 6 shows a partial longitudinal section through an intramedullary nail slotted in the proximal end, with a targeting yoke placed on it;

FIG. 7 shows a partial longitudinal section according to FIG. 6, rotated by 90°;

FIG. 8 shows a partial longitudinal section according to FIG. 7 with an inserted locking element and the targeting yoke removed;

FIG. 9 shows a partial longitudinal section through an intramedullary nail having an unopened slot in the distal part;

FIG. 10 shows a partial longitudinal section according to FIG. 7 with inserted locking elements.

DETAILED DESCRIPTION OF THE PREFERRED EMBODIMENTS

Figure 4:
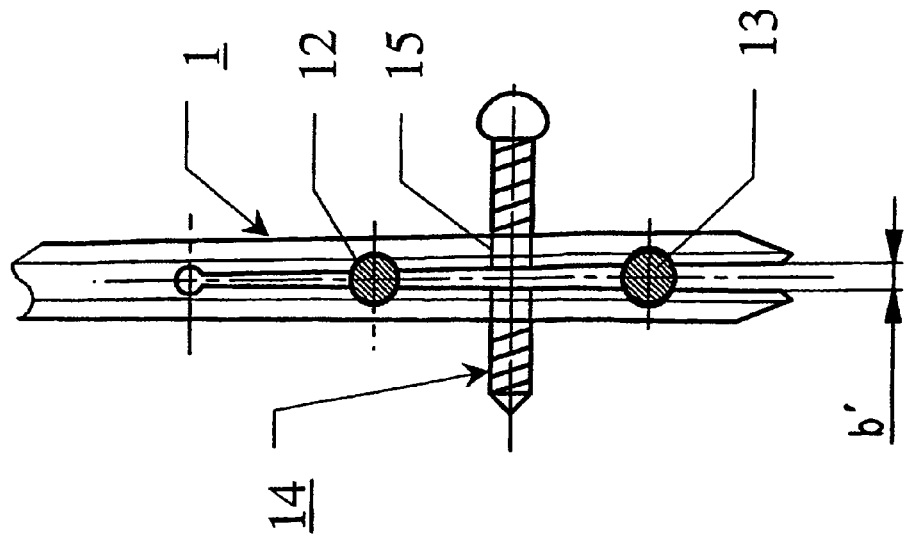
FIG. 4 shows a partial longitudinal section according to FIG. 2 with an additional transverse hole.

The distal end of the intramedullary nail 1, illustrated in FIG. 1, has a longitudinal axis 2, a proximal end 3, a distal end 4, as well as two holes 10,11 extending transversely to the longitudinal axis 2 and at right angles to the plane of the drawing, having diameters d10 and d11, to accommodate the locking elements 12, 13 (FIG. 2) in the form of locking screws, as well as a longitudinal slot 9 with a constant width b and a length $L=(20 \times d10)$, said slot commencing at the distal end 4 and extending parallel to the longitudinal axis 2 and at right angle to the plane of the drawing. At the same time, the diameter d10 of the hole 10 situated closer to the open end of the longitudinal slot 9 is somewhat larger than the diameter d11 of the other hole 11.

In the region between the two holes 10, 11 the longitudinal slot 9 has a width $b=(0.2 \times d10)$, measured in the plane of the drawing.

Both holes 10, 11 have a centre 5, 6, respectively. The longitudinal slot 9 extends from its opening situated at the distal end 4 through both holes 10, 11 slightly further to the proximal end up to the base 8 of the slot in the form of a small hole having a very small diameter. The distance between the base 8 of the slot and the centre 6 of the hole 11 is L2. The greater L2, the more flexible the intramedullary nail.

The distance between the two centres 5, 6 of the two holes 10, 11 is L1. In this embodiment L1 is approx. 30 mm.

Furthermore, the intramedullary nail 1 has a continuous cannulation 7, extending coaxially with the longitudinal axis 2.

As illustrated in FIG. 2, two locking elements 12, 13 can be introduced in the form of bone screws through the two holes 10,11. On this occasion an expansion of the longitudinal slot 9 takes place, so that at the open end of the longitudinal slot its width increases from b to b'>b.

Figure 3:
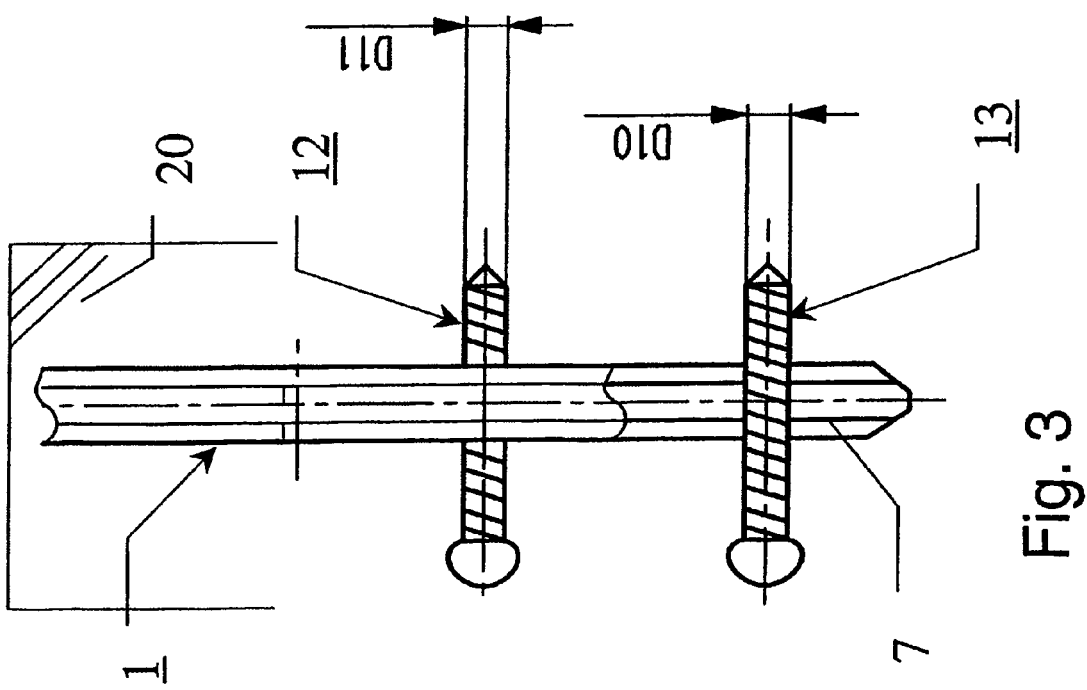
FIG. 3 shows a partial longitudinal section according to FIG. 2, rotated by 90°.

As illustrated in FIG. 3, the shaft of both locking elements 12, 13 has a diameter D10, D11, corresponding to at least 1.1 times, and preferably 1.2 times, the diameter of the corresponding holes 10, 11, so that after the introduction of the two locking elements 12, 13 into the holes 10, 11 the intramedullary nail 1 is elastically expanded in the region of its longitudinal slot 9, as illustrated in FIG. 4.

FIG. 4 illustrates a variation of the intramedullary nail 1, whereby an additional third hole 15 is provided between the two holes 10, 11. The hole 15 is oriented 90° relative to the two other holes 10, 11.

Figure 5:
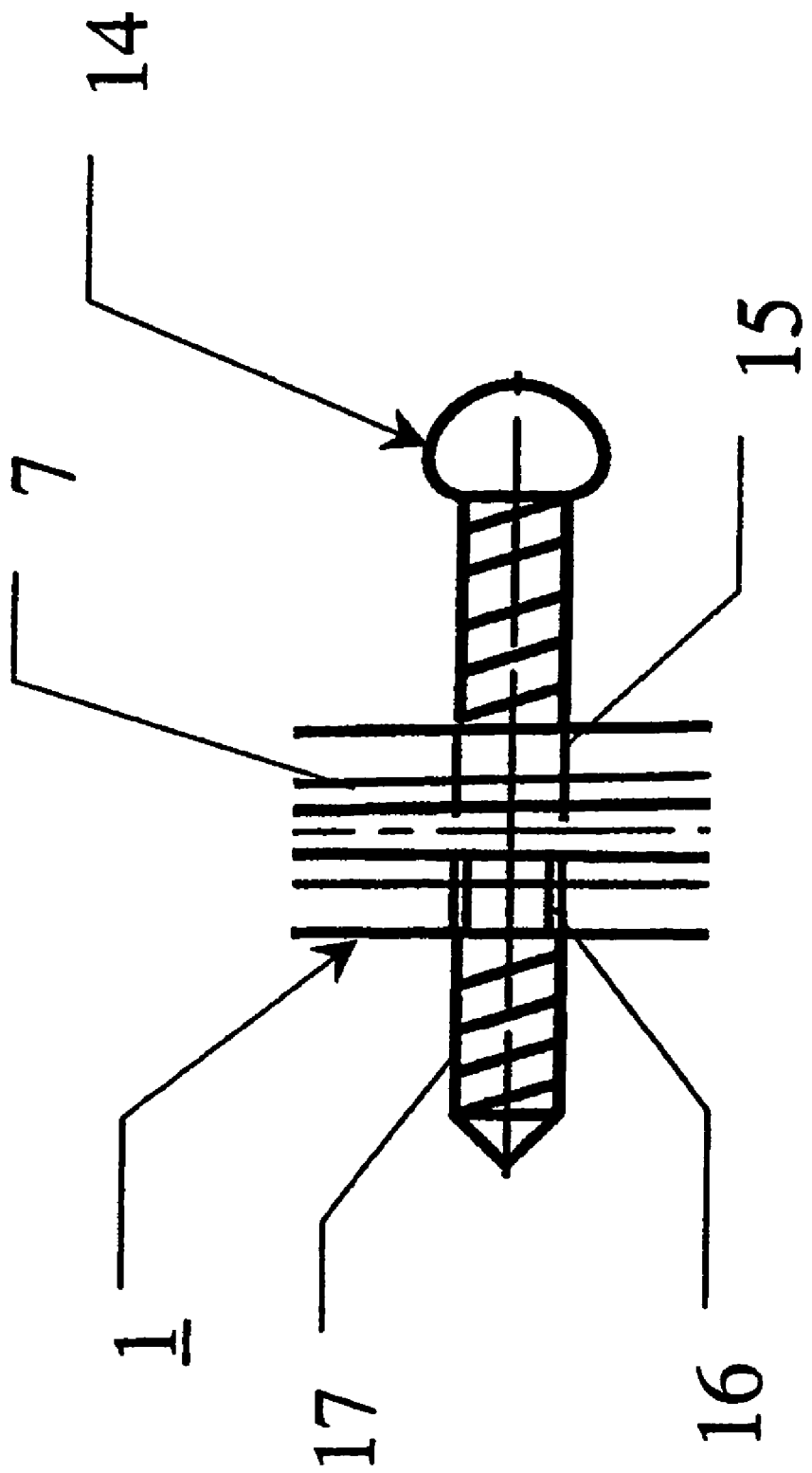
FIG. 5 shows an enlarged section of FIG. 4 in the region of the additional transverse hole.

As it is illustrated in FIGS. 4 and 5, an additional locking element 14, in the form of a locking screw, can be introduced into this additional hole 15. In that segment of the intramedullary nail 1, which is removed from the entry side, an inner thread 16 is provided, that is engaged by the outside thread 17 of the locking element 14, so that the intramedullary nail 1 is held together again in the slotted region by means of the locking element 14.

FIGS. 6-8 illustrate a variation of the intramedullary nail 1, whereby the longitudinal slot 9 is provided not at the distal end 4, but at the proximal end 3 of the intramedullary nail 1. In the case of this embodiment only a single hole 10 is provided to accommodate a single locking element 13 in the form of a locking screw. Otherwise this execution corresponds to that according to FIGS. 1 and 2 for a distally slotted intramedullary nail 1.

As FIG. 6 illustrates, the insertion of the locking element 13 into the hole 10 is carried out with the target yoke 18 in place; on this occasion, the slotted proximal end of the intramedullary nail 1 is expanded, as indicated by arrows 22 (FIG. 7), by the connecting screw 19, so that the locking element 13, having larger dimensions than the hole 10, can be inserted in the hole without any problem. The connecting screw 19 is subsequently released, so that the target yoke 18 can be removed. At the same time the slotted intramedullary nail 1 attempts to contract again at the proximal end 3 as indicated by arrows 21 (FIG. 8), and consequently secures the inserted locking element 13 in the hole 10 in an angularly stable manner.

FIGS. 9 and 10 illustrate a further variation of the intramedullary nail 1, whereby the distal slot 9 is closed at both of its ends, i.e. it is not opened at the distal end 4 of the intramedullary nail 1 as is the case for the embodiments according to FIGS. 1-4. By virtue of this construction, the longitudinal slot 9 expands from its initial width b1 to a width of b1' when the locking elements 12 and 13 are introduced into the holes 10 and 11. Thus the expanded longitudinal slot 9 exerts a permanent clamping force on both locking elements 12 and 13 in the holes 10 and 11, so that they can be securely held in them. The longer L is, the more flexible the intramedullary nail and the simpler its insertion. L1 can be individually adapted to suit and has no influence on the function. The longer L2, the simpler the introduction of the locking elements 12 and 13 and the weaker is their angular stability. Otherwise this execution corresponds to the embodiment according to FIGS. 1-4.

Figure 11:
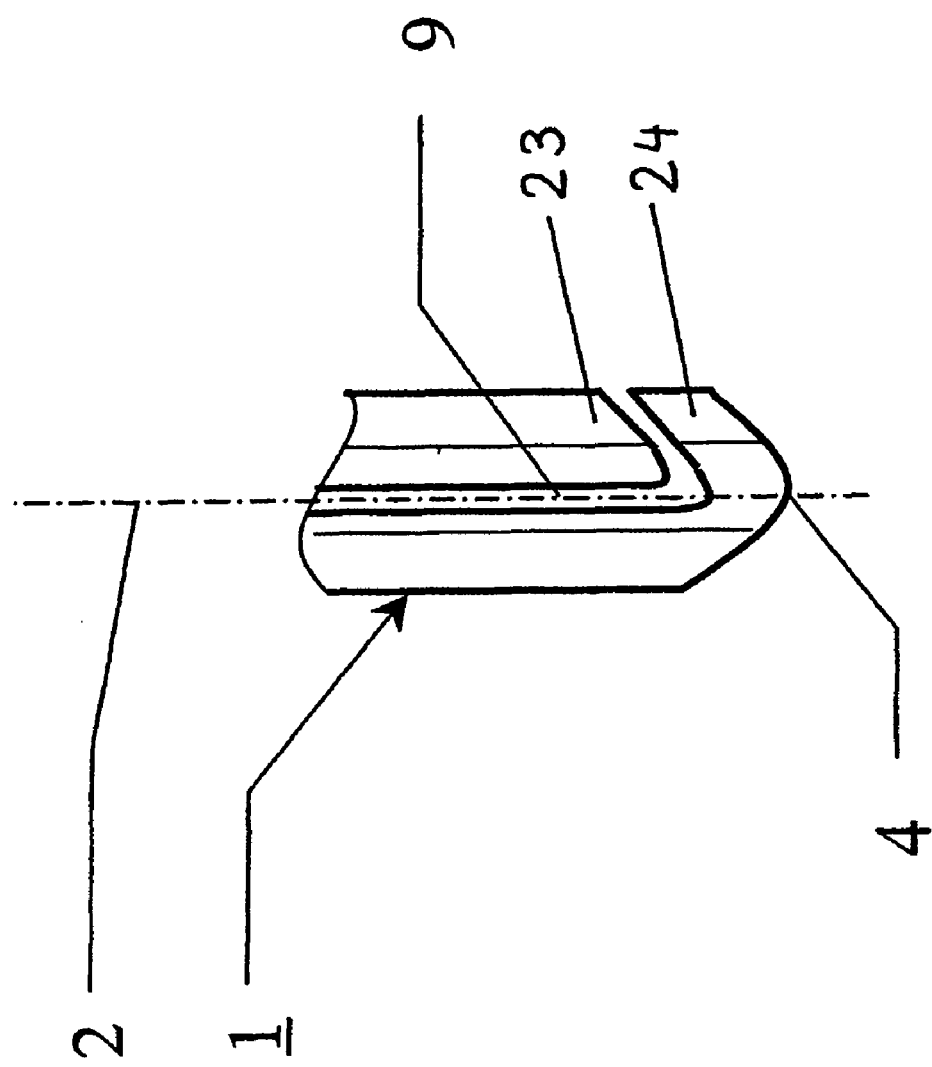
FIG. 11 shows a partial longitudinal section through an intramedullary nail slotted in the distal part, with a slot protection.

FIG. 11 illustrates a further variation of the intramedullary nail 1, whereby the distal slot 9 is not continuously straight, i.e. extends coaxially with the longitudinal axis 2, but is bent shortly before the distal end 4, so that the slot 9 terminates laterally (on the right in this case). By reorienting the slot 9, a protection 23, 24 is realized of the "dovetail" kind that limits the expansion of the slot 9. When expanding the slot 9, the right portion 23 of the intramedullary nail 1 with its oblique end abuts against the correspondingly oblique end 24 of the left bent portion 24 of the intramedullary nail 1, and consequently prevents a further, excessive expansion of the intramedullary nail at its distal part.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. An intramedullary nail comprising:
   a nail body having a central longitudinal axis, a proximal end, and a distal end;
   at least one hole extending through the nail body and having a central hole axis transverse to the longitudinal axis of the nail body, the at least one hole further having a diameter configured to accommodate a locking element, and the central hole axis located in a first plane;
   a longitudinal slot extending through the nail body in the first plane, the longitudinal slot having an unexpanded width b measured perpendicularly to the first plane; and
   an expansion limiting structure integral with the nail body for limiting expansion of the longitudinal slot, wherein the maximum unexpanded width b of the slot is 0.6 times the diameter of the at least one hole, wherein the expansion limiting structure is located at a distal end of the nail body, wherein the expansion limiting structure is different in shape than the at least one hole, and wherein: the expansion limiting structure includes a laterally extending channel open to a distal end of the longitudinal slot, the channel including first and second sides separated from one another by a predetermined distance selected so that, when portions of the nail body spaced from one another by the slot are separated by a desired maximum distance, further separation of the portions of the nail body is prevented by contact between the first and second sides of the channel.

2. The intramedullary nail of claim 1, wherein the maximum unexpanded width b of the slot is 0.5 times the diameter of the at least one hole.

3. The intramedullary nail of claim 1, wherein the nail includes at least two holes extending through the nail body and having central hole axes transverse to the longitudinal axis of the nail body, the at least two holes having two different diameters.

4. The intramedullary nail of claim 3, further comprising at least two locking elements for introduction through the at least two holes, where a first locking element configured for introduction through a hole closer to the distal end of the nail has a diameter greater than the other locking element.

5. The intramedullary nail of claim 1, wherein the longitudinal slot has a length L, where L is at least 10 times the diameter of the at least one hole.

6. The intramedullary nail of claim 5, wherein the width b of the slot is generally uniform over the length L of the slot.

7. The intramedullary nail of claim 1, wherein the nail is substantially hollow along its longitudinal axis.

8. The intramedullary nail of claim 1, further comprising at least one locking element having a diameter.

9. The intramedullary nail of claim 8, wherein the diameter of the locking element is greater than the diameter of the at least one hole.

10. The intramedullary nail of claim 9, wherein the diameter of the locking element is at least 1.1 times that of the diameter of the at least one hole.

11. The intramedullary of claim 8, wherein the intramedullary nail is elastically expanded in the region of the longitudinal slot when the locking element is introduced through the at least one hole.

12. The intramedullary nail of claim 11, wherein the longitudinal slot has a length L, where L is chosen such that during insertion of the locking element through the at least one hole, the intramedullary nail only deforms elastically.

13. The intramedullary nail of claim 1, further comprising an additional transverse hole extending through the nail substantially perpendicular to the first plane.

14. The intramedullary nail of claim 1, wherein the expansion limiting structure is formed by at least one closed end of the nail.

15. An intramedullary nail comprising:
    a nail body having a central longitudinal axis, a proximal end, and a distal end;
    at least one hole extending through the nail body and having a central hole axis transverse to the longitudinal axis of the nail body, the at least one hole further having a diameter configured to accommodate a locking element, and the central hole axis located in a first plane;
    a longitudinal slot extending through the nail body in the first plan, the longitudinal slot bending before reaching the distal end of the nail body and terminating laterally through the nail body to form a laterally extending channel including first and second sides separated from one another that permits expansion of the longitudinal slot up to a predetermined limit, separation of the portions of the nail body beyond the predetermined limit being prevented by contact between the first and second sides of the channel.

16. The intramedullary nail of claim 15, wherein the longitudinal slot has a maximum unexpanded width b that is 0.6 times the diameter of the at least one hole, the width b measured perpendicularly to the first plane.

17. The intramedullary nail of claim 15, wherein the nail includes at least two holes extending through the nail body and having central hole axes transverse to the longitudinal axis of the nail body, the at least two holes having two different diameters.

18. The intramedullary nail of claim 15, further comprising an additional transverse hole extending through the nail substantially perpendicular to the first plane.

\* \* \* \* \*

UNITED STATES PATENT AND TRADEMARK OFFICE
CERTIFICATE OF CORRECTION

| | | |
|---|---|---|
| PATENT NO. | : 8,221,419 B2 | Page 1 of 1 |
| APPLICATION NO. | : 11/365998 | |
| DATED | : July 17, 2012 | |
| INVENTOR(S) | : Frigg et al. | |

It is certified that error appears in the above-identified patent and that said Letters Patent is hereby corrected as shown below:

Title Page:

Item 63 insert

--Related U.S. Application Data

The present application is a Continuation of PCT Patent Application Serial No. PCT/CH2003/000591 filed on August 29, 2003--.

Signed and Sealed this
Ninth Day of October, 2012

David J. Kappos
*Director of the United States Patent and Trademark Office*